United States Patent

Willard et al.

[11] Patent Number: 5,419,774
[45] Date of Patent: May 30, 1995

[54] THROMBUS EXTRACTION DEVICE

[75] Inventors: Lloyd K. Willard, Miltona; Robert L. Cassell, Carlos; Robert J. Robinson, Alexandria; Brian J. Brown, Hanover; Mark J. Whalen, Alexandria; Scott R. Smith, Chaska, all of Minn.

[73] Assignee: SciMed Life Systems, Inc., Maple Grove, Minn.

[21] Appl. No.: 91,337

[22] Filed: Jul. 13, 1993

[51] Int. Cl.$^6$ .............................................. A61B 17/20
[52] U.S. Cl. ........................................ 604/22; 606/159; 606/171
[58] Field of Search ..................... 604/22, 27, 35, 28, 604/43; 606/159, 170, 171

[56] References Cited

U.S. PATENT DOCUMENTS

| | | | |
|---|---|---|---|
| Re. 33,258 | 7/1990 | Onik et al. | 606/171 |
| 3,614,953 | 10/1971 | Moss | 128/305 |
| 3,844,272 | 10/1974 | Banko | 128/2 B |
| 3,937,222 | 2/1976 | Banko | 128/305 |
| 3,945,375 | 3/1976 | Banko | 128/6 |
| 4,020,847 | 5/1977 | Clark, III | 128/305 |
| 4,030,503 | 6/1977 | Clark, III | 128/304 |
| 4,493,694 | 1/1985 | Wuchinich . | |
| 4,516,398 | 5/1985 | Wuchinich . | |
| 4,589,412 | 5/1986 | Kensey . | |
| 4,620,547 | 11/1986 | Boebel | 128/754 |
| 4,631,052 | 12/1986 | Kensey . | |
| 4,646,738 | 3/1987 | Trott | 128/305 |
| 4,664,112 | 5/1987 | Kensey et al. . | |
| 4,669,469 | 6/1987 | Gifford, III et al. | 128/305 |
| 4,676,249 | 6/1987 | Arenas et al. | 128/657 |
| 4,678,459 | 7/1987 | Onik et al. . | |
| 4,679,558 | 7/1987 | Kensey et al. . | |
| 4,681,106 | 7/1987 | Kensey et al. . | |
| 4,696,667 | 9/1987 | Masch | 604/22 |
| 4,700,705 | 10/1987 | Kensey et al. . | |
| 4,728,319 | 3/1988 | Masch | 604/22 |
| 4,729,763 | 3/1988 | Henrie | 604/22 |
| 4,732,154 | 3/1988 | Shiber | 128/305 |
| 4,747,821 | 5/1988 | Kensey et al. . | |
| 4,749,376 | 6/1988 | Kensey et al. . | |
| 4,771,774 | 9/1988 | Simpson et al. | 128/305 |
| 4,784,636 | 11/1988 | Rydell . | |
| 4,819,634 | 4/1989 | Shiber | 128/305 |
| 4,819,635 | 4/1989 | Shapiro . | |
| 4,846,192 | 7/1989 | MacDonald Stuart G. | 128/752 |
| 4,857,045 | 8/1989 | Rydell . | |
| 4,857,046 | 8/1989 | Stevens et al. . | |
| 4,886,061 | 12/1989 | Fischell et al. . | |
| 4,913,698 | 4/1990 | Ito et al. . | |
| 4,917,085 | 4/1990 | Smith | 606/159 |
| 4,926,858 | 5/1990 | Gifford, III et al. . | |
| 4,957,482 | 9/1990 | Shiber . | |
| 4,979,939 | 12/1990 | Shiber | 606/159 |
| 4,979,951 | 12/1990 | Simpson | 606/159 |
| 4,994,067 | 2/1991 | Summers | 604/22 |
| 4,998,919 | 3/1991 | Schnepp-Pesch et al. . | |
| 5,007,896 | 4/1991 | Shiber | 604/22 |

(List continued on next page.)

FOREIGN PATENT DOCUMENTS 9214413 9/1992 WIPO ................................ 604/22

OTHER PUBLICATIONS

Brief Communications; Transcatheter Aspiration of Intracoronary Thrombus After Myocardial Infarction; Stephen E. Brown et al.; pp. 688–690.

(List continued on next page.)

Primary Examiner—John D. Yasko
Assistant Examiner—Frank Wilkens, III
Attorney, Agent, or Firm—Nawrocki, Rooney & Silvertson

[57] ABSTRACT

This invention is a method and device for quickly removing thrombus from the vascular system, particularly from a saphenous vein graft which can have highly organized thrombus over its entire length. Thrombus is pulled into a chamber at the distal end of the thrombus extraction device as a result of negative pressure, a severing mechanism severs the portion of the thrombus that is in the chamber, and fluid under pressure is supplied to transport and dilute the blood and thrombus, which renders the thrombus more manageable and reduces the blood loss to the patient.

12 Claims, 8 Drawing Sheets

U.S. PATENT DOCUMENTS

| | | |
|---|---|---|
| 5,011,488 | 4/1991 | Ginsburg . |
| 5,030,201 | 7/1991 | Palestrant . |
| 5,042,984 | 8/1991 | Kensey et al. . |
| 5,052,404 | 10/1991 | Hodgson ............................ 128/772 |
| 5,059,178 | 10/1991 | Ya . |
| 5,071,425 | 12/1991 | Gifford, III et al. . |
| 5,074,841 | 12/1991 | Ademovic et al. .................... 604/22 |
| 5,085,662 | 2/1992 | Willard .............................. 606/159 |
| 5,087,265 | 2/1992 | Summers . |
| 5,092,839 | 3/1992 | Kipperman . |
| 5,092,873 | 3/1992 | Simpson et al. . |
| 5,100,424 | 3/1992 | Jang et al. . |
| 5,100,425 | 3/1992 | Fischell et al. ...................... 604/22 |
| 5,106,364 | 4/1992 | Hayafuji et al. ..................... 606/171 |
| 5,114,399 | 5/1992 | Kovalcheck ......................... 604/22 |
| 5,181,920 | 1/1993 | Mueller et al. ....................... 604/22 |
| 5,250,059 | 10/1993 | Andreas et al. ...................... 606/171 |
| 5,344,395 | 9/1994 | Whalen et al. ...................... 606/159 |

OTHER PUBLICATIONS

Clinical Results; Apr. 1990; Rolf W. Guenther et al.; pp. 271–273.

The American Journal of Cardiology, vol. 60; Aug. 1, 1987; Transcatheter Aspiration of A Thrombus in an Aortocoronary Saphenous Vein Graft; Robert C. Feldman; pp. 379–380.

Aspiration Catheter for Percutaneous Thrombectomy: Journal of Thoracic & Cardiovasc Surg. (1962) 44; Endovascular Suction Catheters; For Thrombectomy and Embolectomy; W. Andrew Dale; pp. 557–558.

Angiology 12 (1961); The Roto-Drill, A New Instrument for Thromboendarterectomy; B. G. P. Shafiroff, M.D.; pp. 316–319.

Surgery Its Principles and Practice by Various Authors; 1910; pp. 96–99.

Medical Progress; Surgical Clinic on the Catherization of Arteries by Professor Severeanu (from Bucharest, Rumania); pp. 1–4.

Stereotact Funct. Neurosurg 1989:53:77–84; Stereotactic Aqua Stream and Aspirator for Hypertensive Intracerebral Hematoma; Haruhide Ito et al; pp. 77–84.

Neurosurgery; vol. 25, No. 3, 1989; Mechanical Aspiration of Hematomas in an in Vitro Mode; Howard H. Kaufman et al.; pp. 347–350.

Arch Ophthal; vol. 86, Nov. 1971; Experimental Vitrectomy; Instrumentation and Surgical Technique; Gholam A. Peyman et al.; pp. 548–551.

Surgical Dynamics; Nucleotome System; Automated Percutaneous Lumbar Discectomy; Diagnosis: Treatment of Choice: Automated Percutaneous Lumbar Discectomy; 1990.

Gunther 1992 Device Rotating Basekt; WO 92/03098; P 40 25 825.4 (OE).

The Britain Medical Journa; Sep. 21, 1097; Operation for Embolus; p. 712.

THROMBUS EXTRACTION DEVICE

BACKGROUND OF THE INVENTION

The field of this invention is a method and device for removing thrombus from the peripheral or coronary vascular system and particularly from saphenous vein grafts (SVG) that were grafted during coronary artery bypass surgery.

Saphenous veins, which are large leg veins, are extracted and implanted to bypass diseased arteries in the surgical procedure of coronary artery bypass graft (CABG). Although saphenous vein grafts usually extend the life of the patient and improve the quality of life, these results endure for only a limited time. Saphenous vein grafts will frequently develop flow restrictions after about 8 years. When these restrictions occur, they are the result of both atherosclerosis and thrombosis.

There is no current well-accepted procedure for removing the thrombus, which sometimes extends the entire length of the SVG or is formed as thrombus segments within the SVG. The degree of organization of the thrombus in the SVG is greatest at its anastomoses or at the ends of the thrombus segments, and in these locations the thrombus is better organized and thus more resistant to removal. It is highly desirable that the thrombotic material that occupies the lumen of the SVG vessel be removed prior to invasive treatment of the underlying stenotic lesion. The thrombosis that occurs and finally stagnates the blood flow is the direct effect of the slowed velocity of the blood flow due to the stenosis.

When an SVG becomes clogged, there are two therapeutic options available: add an additional graft using the other saphenous vein (when available), or remove the thrombus with chemical thrombolytic drugs or vacuum extraction and treat the clogged vessel with therapies such as stents or balloon angioplasty. Because the SVGs are very fragile, these therapeutic methods have had severe limitations in the past.

The disadvantage of using a chemical thrombolytic drugs is their very slow dissolution rate, requiring the patient to be non-ambulatory and retained in intensive care during the systemic use of the thrombolytic drugs. The worst of the many complications may be cerebral bleeding. Additionally, the patient may be required to remain in a prolonged unstable state during a life-threatening period.

Vacuum extraction catheters, on the other hand, require the use of very large catheters having very large bores and diameters. These large sizes are dictated by the propensity of the blood and the thrombus to coagulate and block the lumen of the extraction catheters. Additionally, this method removes a large amount of blood during the process of extracting the clot.

When a thrombus originally forms in the coronary arteries, it has high viscosity fluid components with a minimal fibrous matrix contained in the fluid. The fibrous matrix tends to structurally bind the thrombus together; however, it can be easily separated.

In comparison, thrombus occurring in nonpatent saphenous vein grafts will tend to be more organized at the anastomotic sites or at the two ends of the thrombus segment and be relatively less organized within the centers. Within this relatively less organized matrix there will also be organized particles.

The problem of thrombosis is also present in the arterial vascular; however, the volume and degree of organization vary according to location. Thrombosis formed in coronary arteries is much smaller in volume and less organized. The peripheral and cerebral vascular systems also have varying degrees and amounts of thrombotic and stenotic occurrence. The thrombotic occurrence in larger vessels frequently will have a characteristically large and organized thrombotic deposit near a stenotic site.

Several approaches have been tried for removing obstructions and thrombus in the vascular. An early approach is recorded in the British Medical Journal in 1907. Dr. W. Sampson Handley passed a flexible tube into the femoral artery, connected the proximal end to an aspirator, and removed soft blood clots. He also introduced a ureteral catheter along the common femoral, the external iliac, and the common iliac artery until it reached the bifurcation of the abdominal aorta. Handley then sent a forcible stream of saline through the catheter to dislodge clot that returned through the divided end of the profunda.

Another approach for removing obstructions can be found in U.S. Pat. No. 5,114,399, which discloses a catheter for removing obstructive material from a body cavity or lumen. The invention of this patent is a catheter device and method for removing obstructive material using a high-speed rotating blade assembly that is forced into contact with the obstructive material and a homogenizing means that functions to disintegrate the cored material so that it can be aspirated away. This catheter has a blade assembly that rotates at 5,000 R.P.M. and that includes a cylindrical-shaped coring blade that cores into the obstructive material and homogenizing blades that dice the cored material into smaller pieces. Assuming that the blade assembly has an outer diameter of 0.04 inches, then the outer surfaces of the knife blade apparatus have a speed of over 700 inches per second. The cylindrical-shaped portion of obstructive material is forced through the cylindrical passage defined by the coring blade. The rotating blade assembly also includes diametrically extending blades that homogenize the obstructive material which is then aspirated out of the cylindrical passage. Irrigation fluid is pumped to the tip of the catheter through one lumen and aspirated out along with the homogenized material through another lumen. The high speed rotating blade assembly is in contact with the patient's blood stream.

In the '399 device fluid is in contact with high-speed moving components that could cause the blood in the proximity of the catheter to undergo hemolysis due to the localized shear stresses and the mixing due to induced fluid vortexing. Hemolytic effects in the fluid retained within the body of the surgical device would be of no consequence, but any lysed blood remaining in the circulatory system may result in thrombogenesis within the vascular of that or other organs of the body. The '399 device is designed for accessing and removing atheroma or obstructive materials, particularly stenotic materials, which are present behind the intimal layer of the vessel. Removal of the intimal layer is opposite the objective of the thrombus extraction device described as the device and method of this invention.

U.S. Pat. No 4,979,951 discloses an atherectomy device for removing atheroma in an arterial vessel. The device includes a longitudinal housing having a cutout extending longitudinally on one side of the housing. Within the housing there is a rotating cup-shaped cutter that can be advanced along the length of the housing. An inflatable balloon is secured to the housing on the side opposite the cutout such that when the balloon is inflated the cutout is forced against the wall segment containing the atheroma that is to be removed. When the cup-shaped cutter is filled with material from the atheroma, the atherectomy device is removed from the patient and then replaced if more material is to be removed. The invention of the '951 patent involves pressing the open-sided housing against the side of the blood vessel to isolate the atheroma being removed from its environment. The device is not directed to the task of removing thrombus but rather to removing atheroma which presents different problems and requires solutions different than that presented in this current application. The disadvantage of this system is that the cutter is exposed to the vessel wall and removes a portion of the intima layer in order to remove the atheroma formed therein. In addition, once the cutter cup is full, the device must be removed and emptied before continuing with the procedure.

For the foregoing reasons there is a need for a device and method for removing thrombus from saphenous vein grafts or from peripheral or coronary arteries at a controlled rate with a device that quickly removes thrombus but does not remove the intimal layer of the vessel wall, that does not expose the vessel wall directly to cutters, that does not have to be removed during the thrombus extraction procedure, and that does not clog.

SUMMARY OF THE INVENTION

The present invention is directed to a device and method that quickly and effectively removes thrombus from the vascular system. This device does not become clogged with thrombus, minimizes damage to the patient's blood and vessel, and results in minimal blood loss. Furthermore, because the device does not collect thrombus in a receptacle but transports cut pieces distally using an irrigation fluid, the device does not have to be removed during the thrombus extraction procedure.

When using the device in a saphenous vein graft, the device is guided without the aid of a guide wire into the graft through a guide catheter or other similar introductory device such as that disclosed in copending application Ser. No. 08/035,379 and U.S. Pat. No. 5,219,335. This introduction method avoids the possible dislodging of thrombus prior to initiating the process-dislodging that could occur if a guide wire were used.

According to this invention the rate at which material is pulled into the chamber at the distal end of the catheter is controlled by the pressure exerted on the irrigation solution, the level of the vacuum pressure supplied to the discharge lumen, and the timing and speed of the cutter stroke. Additionally, this invention defines a method of thrombus removal in saphenous vein grafts and in other vascular locations using a relatively small device that is not susceptible to clogging, that is easily manipulated, and that accomplishes its objective quickly.

Saphenous vein grafts vary in length from one and one-half inches to five inches and the procedure should be completed in less than two minutes. Thus, the process must be capable of advancing from one anastomosis of a saphenous vein graft to either the other anastomosis or to an atherosclerotic occlusion within the graft, removing all thrombus as it advances, in less than two minutes. The advancing rate through the saphenous vein graft will be slower at the anastomoses or at the end caps of the thrombus segment than in the intermediate section where the thrombus is less organized. The technician performing the procedure manually controls the advancing rate of the device through the saphenous vein graft. The removal rate of thrombus is observable through visual and audible feedback. The technician can visually observe the quantity of thrombus particles present in the fluid that is being extracted through a transparent tube leading to a fluid collection reservoir, and changes in this rate are noticeable. Also, changes in the quantity of thrombus particles present in the fluid being extracted results in a change in the sound of the flowing fluid. This sound can be amplified and used to assist the technician in properly controlling the rate of advancing through the saphenous vein graft. The thrombus extraction is complete when the vessel segment has been purged of thrombus. The technician will observe a significant decrease in the presence of thrombus particles when the device reaches the distal end of the thrombus segment. If the device reaches a nearly closed atherosclerotic occlusion, it may be necessary to remove the thrombus extraction device, dilate or extract a stenotic region of the SVG, then reinsert the thrombus extraction device to remove the next thrombus segment.

DETAILED DESCRIPTION OF THE PREFERRED EMBODIMENT

Figure 1:
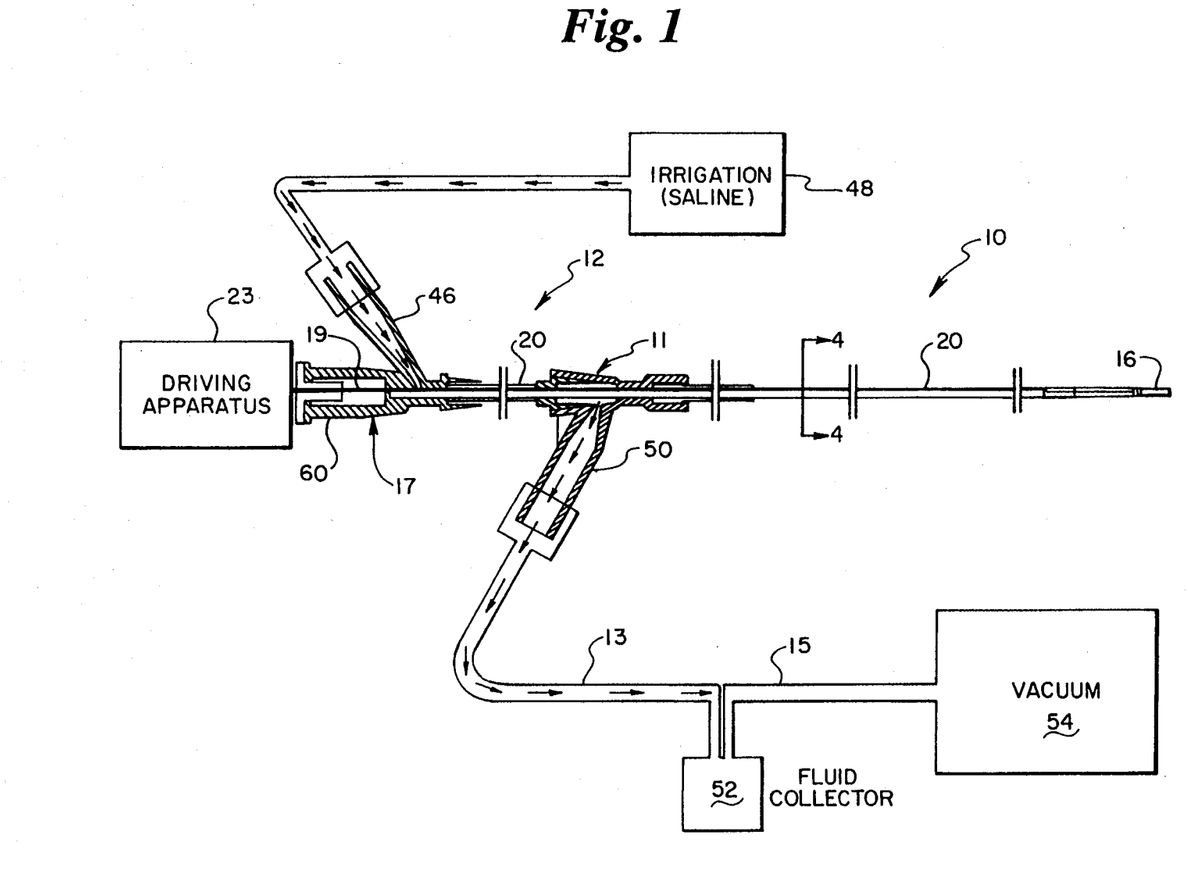
FIG. 1 is a cross-sectional side view of 35 the preferred embodiment of the thrombus extraction device including the manifold system located at the proximal end.

FIGS. 1 through 9 show the basic construction of the preferred embodiment of the device. FIG. 1 is an overall cross-sectional side view of the entire thrombus extraction device 10 including the manifold system 12 which is located at the proximal end. The manifold system 12 includes a distal manifold 11 having a port 50 through which a vacuum or negative pressure is applied to lumen 30. The port 50 is connected through a conduit 13 to a fluid collector 52 which is connected through a conduit 15 to a vacuum pump 54. The vacuum pump 54 can be regulated and adjusted to control the negative pressure. Vacuum pump 54 must develop a minimal negative pressure of 20 inches of mercury and preferably operates in the range of 23–25 inches of mercury. A proximal manifold 17 is connected to distal manifold 11 by the multi-lumen catheter body 20. A support tube 19 (FIG. 4) that accommodates and supports the proximal end of the cutter core wire 21 exits through the proximal end of proximal manifold 17. A driving apparatus 23 is connected to the cutter core wire 21 and functions to reciprocate, or optionally rotate, the cutter 40 (FIG. 7) at the appropriate time in the extraction procedure. Irrigation fluid such as saline is stored in a fluid supply means 48 from which it is pumped through port 46 of the proximal manifold 17. Fluid under pressure flows from port 46 into lumen 24 of the multi-lumen catheter body 20. The pressure of the fluid flowing through the catheter body should be variable from 4 to 100 p.s.i.

The distal tip 16 of the thrombus extraction device 10 must be sufficiently soft and flexible to avoid excessive damage during its presence in the vascular system. It is important that the location of the thrombus extraction device within the vessel must be observable at all times using fluoroscopy. Radiopaque markers 18 (see FIG. 7) may be placed on the device for angiographic tracking. An optional coating, that resists initial protein absorption required to start blood coagulation, may be applied to the outer surface of the thrombus extraction device 10. The thrombus extraction procedure must be sufficiently fast to prevent excessive stress to the patient caused by the loss of blood flow.

Figures 7, 7B, 7C:
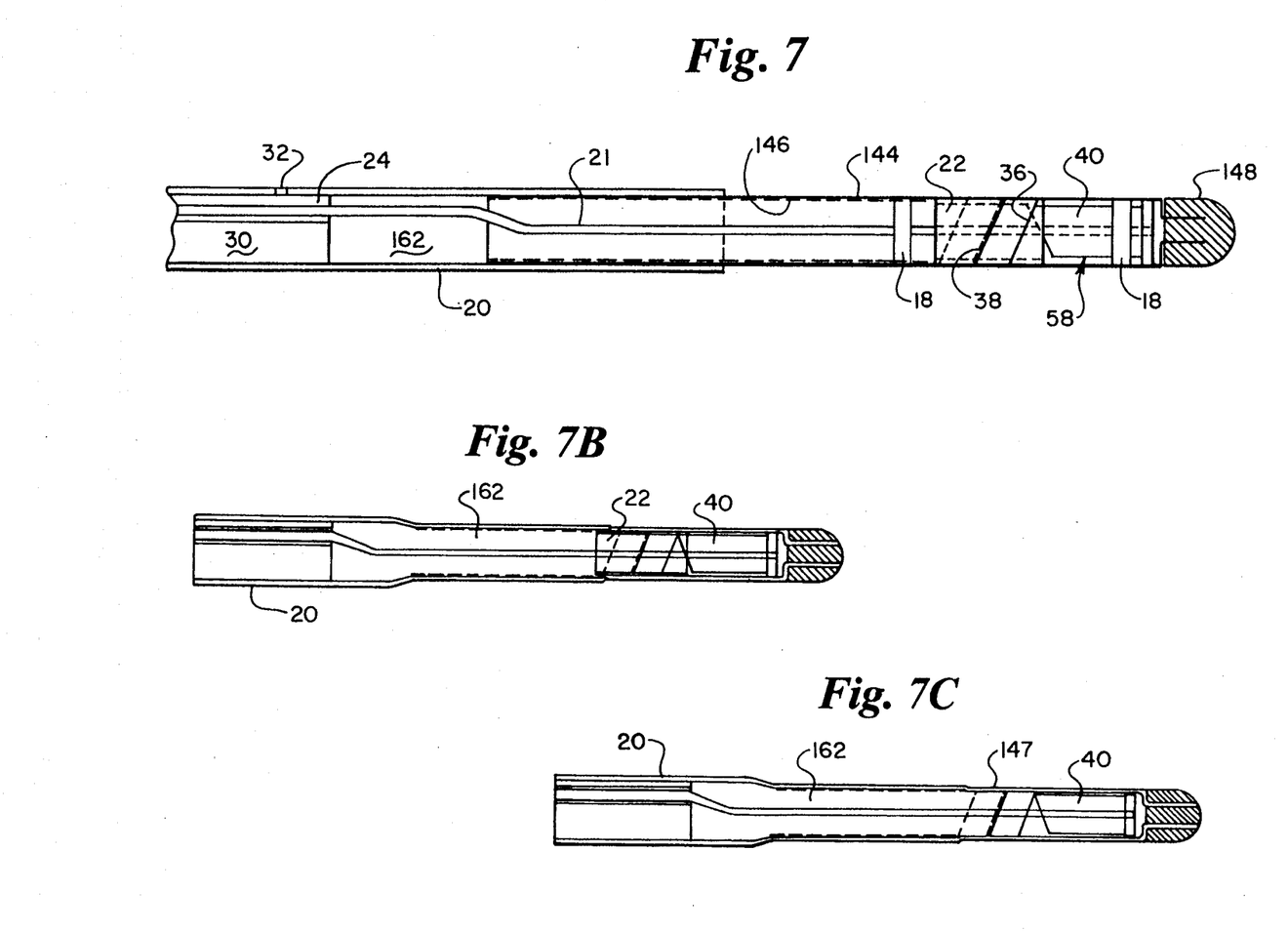
FIG. 7 is a cross-sectional view of the distal end portion of the preferred embodiment of the thrombus extraction device.
FIG. 7B is a cross-sectional view of the distal end portion of an alternate version of the embodiment shown in FIG. 7.
FIG. 7C is a cross-sectional view of the distal end portion of another alternate version of the embodiment shown in FIG. 7.

The thrombus extraction device 10 consists of a multi-lumen catheter body 20 having a distal housing 22 which has an atraumatic distal tip 16 (FIGS. 1 and 7). The catheter body can be either homogeneous or non-homogeneous in composition or geometry. For example, a homogeneous body may be made of a single material or have uniform geometry throughout its length to impart uniform structural and flexural characteristics throughout its length, or the body can be nonhomogeneous with varying structural properties, compositions, or geometry along its length. A nonhomogeneous catheter body may be made partially or entirely of composite materials and may comprise, for example, a relatively more rigid section which functionally provides for the distal housing 22.

The multi-lumen catheter body 20 is about 57.75 inches long and has an outside diameter of about 0.040 to 0.080 inches. The multi-lumen catheter body 20 includes a first lumen 24 (FIG. 4) that functions to supply fluid to the distal section of the thrombus extraction device. A flexible elongated member 28 comprising the support tube 19 and cutter core wire 21 extends through first lumen 24. The cutter core wire 21 functions to transmit longitudinal or optional rotary movement from the driving apparatus 23 to cutter 40. The cutter 40 and cutter core wire 21 together form an elongated cutting assembly 58. A second, larger lumen 30 is used as a return route for fluid and thrombotic debris. The first lumen 24 has an inside radial height of about 0.010 to 0,030 inches, and the second lumen has an inside radial height of about 0.020 to 0.050 inches. Lumens 24 or 30 may be noncircular or circular in cross-sectional geometry.

The manifold assembly 12 is located at the proximal end of the multi-lumen catheter body 20. A first port 46 of the manifold assembly 12 is connected to a fluid supply means 48 which is in fluid communication with the first lumen 24. A second port 50 is connected to a fluid collector 52, which is connected to a vacuum pump 54. The second port 50 is in fluid communication with the second lumen 30. The proximal end of elongated cutter assembly 58 passes through a third port 60. A battery-operated power supply unit 62 for supplying energy for reciprocating or optional rotary motion of the cutter assembly 58 is located proximally of third port 60.

Figure 2:
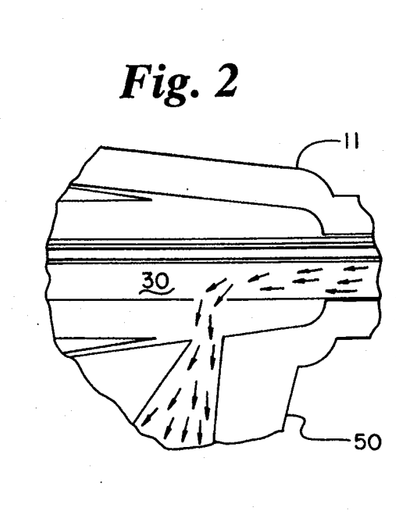
FIG. 2 is an enlarged cross-sectional view of a section of the distal manifold including arrows that represent the flow of fluid from the distal end of the thrombus extraction device into the fluid collector.

FIG. 2 is an enlarged cross-sectional view of a section of the distal manifold 11 including arrows that represent the flow of fluid in lumen 30 from the distal end of the thrombus extraction device through port 50 and into the fluid collector 52.

Figure 3:
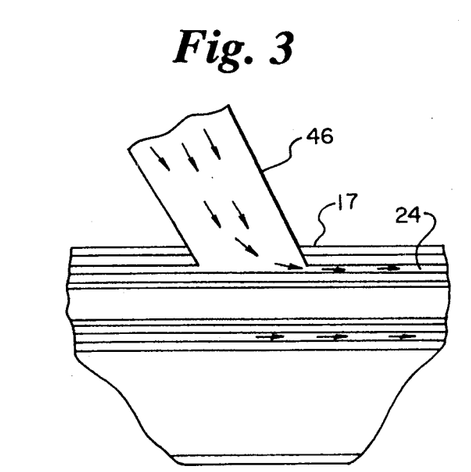
FIG. 3 is an enlarged cross-sectional view of a section of the proximal manifold including arrows 10 that represent the flow of fluid through the first lumen.

FIG. 3 is an enlarged cross-sectional view 35 of a section of the proximal manifold 17 including arrows that represent the flow of fluid through port 46 into the first lumen 24.

Figure 4:
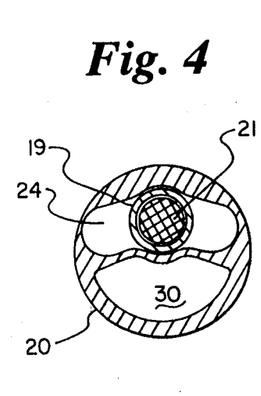
FIG. 4 is an enlarged cross-sectional view of the multi-lumen catheter body taken along lines 4—4 of FIG. 1.

FIG. 4 is an enlarged cross-sectional view of the multi lumen catheter body 20 taken along lines 4—4 of FIG. 1. In this view the first lumen 24 through which the saline fluid flows in the distal direction also houses the cutter core wire 21 that is contained within support tube 19. The vacuum pump 54 which is the source of negative pressure is connected to the second lumen 30 through port 50.

Figure 5:
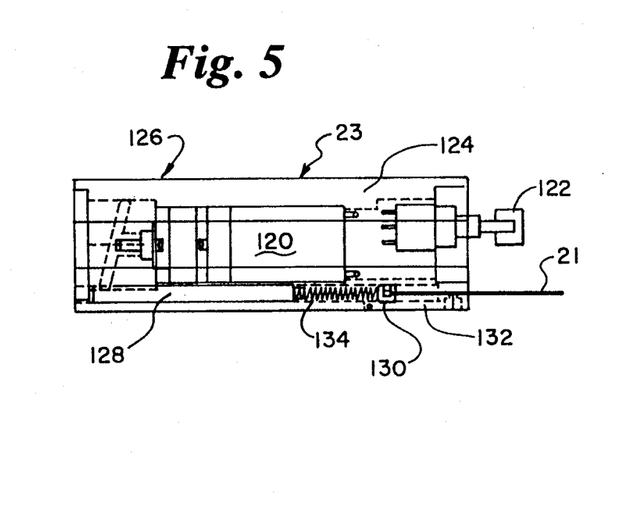
FIG. 5 is a top view of the driving apparatus which is connected to the cutter core wire.

FIG. 5 is a view of the driving apparatus 23 which is connected to the cutter core wire 21 that transmits reciprocal motion to the cutter 40 at the appropriate time in the thrombus extraction process. The driving apparatus 23 includes a housing 124 in which is mounted an electric motor 120 that is controlled by a switch 122. The motor 120 drives a cam 126 that cooperates with a cam follower rod 128. A catheter actuation coupling 130 is mounted for sliding action in a groove 132. A compression spring 134 extends between the cam follower rod 128 and the catheter actuation coupling 130 to insure good contact between the cam 126 and the cam follower rod 128 and to provide some resiliency to the system. The cutter core wire 21 is connected to catheter actuation coupling 130. Driving apparatus 23 can be any mechanical apparatus, such as a spring-operated device, or any electromechanical apparatus that imparts reciprocating or rotary motion, either entirely or in combination or intermittently.

Optionally, other embodiments of the device are contemplated for use in special situations, in which the application of vacuum pressure and injection fluid as well as mobilizing the cutter are all 35 controlled manually. Such manual control could be readily applied to the thrombus extraction device when used to extract acute thrombus, which is highly unorganized in nature. In this procedure, the thrombus extraction device is advanced into the thrombus, vacuum pressure is applied to lumen 30, and the cutter is manually reciprocated, severing the thrombus as it is aspirated into the windows 36 and 38. With the windows in a closed position, irrigation fluid is then supplied under pressure to the distal portion of the catheter through lumen 24 to flush the clot and fluid proximally through lumen 30. In this example the vacuum source and the source of pressurized irrigation fluid could separately be supplied by hand-operated syringes.

Figure 6:
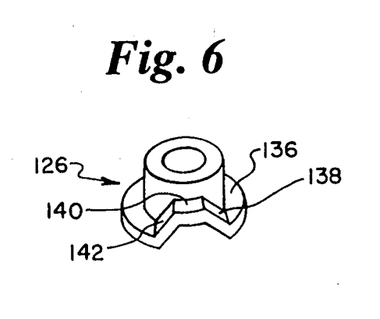
FIG. 6 is a perspective view of the cam of the driving apparatus.

FIG. 6 is a perspective view of the cam 126. The cam 126 includes a cutter open dwell section 136, a cutter close ramp section 138, a cutter closed dwell section 140, and a cutter open ramp section 142. As is apparent from this drawing the cutter is open for approximately 300° of its cycle and is closed for only about 20° of its cycle. The other 40° of the cycle is transitional between completely open and completely closed operations. The action of the cam causes the windows to be partially or entirely open for about 80 percent of the cycle time and closed for about 20 percent of the cycle time. Other ratios of open to closed may be used as long as effective thrombus aspiration and cutting action are maintained.

The speed at which the cutter moves, in this embodiment, is critical to the proper operation of this device. It has been found that cutter speeds below five (5) inches per second are unacceptable, and cutter speeds in the range of five (5) to one hundred fifty (150) inches per second are acceptable. When cutter speeds below five (5) inches per second are used, the thrombus is crushed rather than severed during the process, procedural time is excessives and the propensity for embolizing particles that escape from the catheter is increased. When speed in excess of one hundred fifty inches per second is used, excessive stresses are placed on the components, and migration time for thrombus to reach the housing is inadequate. In the preferred embodiment the cutter 40 has a stroke length of about 0.060 inches, which at the extremes of the above cutter speed range will require 0.012 seconds and 0.0004 seconds. Thus, by restricting the cutting speed to the range of 5 inches to 150 inches per second and utilizing a relative short cutting stroke of about 0.060 inches, a clean severing of the thrombus that has been pulled into the chamber housing is attained, and hemolysis is very nearly eliminated or minimized as a result of the relatively slow cutter speed, the extremely short period of time that the cutter is moving, and the limited exposure of moving components to the blood. The cutter may have a stroke length in the range of 0.030 inches to 0.150 inches.

FIG. 7 is a cross-sectional view, of the distal end portion, of the preferred thrombus extraction device 10. The distal end of the multi-lumen catheter body 20 has been bored out such that the first lumen 24 and the second lumen 30 merge into a single lumen 162. A single-lumen tube 144 that has been shrunk around a coil spring 146 is dimensioned to telescope within single lumen 162 and be secured thereto by bonding or the like. The coil spring 146 functions to provide structural support to the distal end of the thrombus extraction device 10. The outside diameter of the distal housing 22 corresponds to the inside diameter of the single-lumen tube 144 so that the housing 22 can be telescoped within the tube 144 35 and secured thereto by bonding or the like. The distal end of the coil spring 146 is attached to the proximal edge of the distal housing 22. The unreinforced portion of the single-lumen tube 144 continues past the distal end of the distal housing 22 and terminates in a closed end tip 148. The closed end tip 148 can be formed by necking the tube 144 and forming an epoxy tip around the pinched end, the proximal end of which serves as a stop for the distal end of cutter 40. The closed end tip 148 has a smooth contour to minimize damage to the vessel wall that it encounters. The cutter 40 is housed in the section of the single-lumen tube 144 near the distal end of the distal housing 22 and proximal the closed end tip 148. Alternately, single lumen 162 can be extended to functionally replace single-lumen tube 144 (FIG. 7B). Similarly, catheter body 20 can be composed partially or entirely of a nonhomogeneous material, such as a composite, and may comprise a relatively more rigid section 147 which functionally provides for the distal housing 22 (FIG. 7C).

The first lumen 24 provides a passageway for the flexible elongated member 28. In the preferred embodiment, the core wire 21 of the flexible elongated member 28 is made from a suitable material such as stainless steel wire. The cutter core wire 21 is about 67 inches long and has an outside diameter of about 0.012 inches. The cutter core wire may be of a shape other than round in cross section. The preferred embodiment, which utilizes longitudinal reciprocal movement of the cutter, requires that the cutter core wire has an $I_x$ value (inertial constant based on shape) no less than $4.17 \times 10^{-13}$ inches$^4$ and no greater than $3.0 \times 10^{-9}$ inches$^4$. For alternate rotation of the cutter 40 by cutter core wire 21, the shape of the 35 cutter core wire may be of any shape such that the the inertial constant in the x direction ($I_x$) is within inertial constant in the y direction ($I_y$) divided by the range of $$0.6 \leq \frac{I_x}{I_y} \leq 1.4$$

Factoring in the effect of modulus of elasticity (E), the same ranges apply:

$$0.6 \leq \frac{E_x I_x}{E_y I_y} \leq 1.4$$

In the above equations the following definitions apply:
 $I_x$=Moment of inertia when the x axis is held stationary and flexure occurs in the direction of the y axis.
 $I_y$=Moment of inertia when the y axis is held stationary and flexure occurs in the direction of the x axis.

The following table includes examples of Moment of Inertia (I) for round wire, where $I_x = I_y$:

| Moment of Inertia (Round | |
|---|---|
| Diameter (in.) | Moment of Inertia (in.^4) (I) |
| 0.003 | 3.98E-12 |
| 0.004 | 1.26E-11 |
| 0.005 | 3.07E-11 |
| 0.006 | 6.36E-11 |
| 0.007 | 1.18E-10 |
| 0.008 | 2.01E-10 |
| 0.009 | 3.22E-10 |
| 0.010 | 4.91E-10 |
| 0.011 | 7.19E-10 |
| 0.012 | 1.02E-09 |
| 0.013 | 1.40E-09 |
| 0.014 | 1.89E-09 |
| 0.015 | 2.49E-09 |

The following table includes example of Moment of Inertia (I) for flat wire having cross section dimensions of x and y.

| | Moment of Inertia (Rectangular Wire) | | | | | | | |
|---|---|---|---|---|---|---|---|---|
| | y (Height) | | | | | | | |
| x (base) | 0.002 | 0.004 | 0.006 | 0.008 | 0.010 | 0.012 | 0.014 | 0.015 |
| 0.005 | 3.33 E-12 | 2.67 E-11 | 9.00 E-11 | 2.13 E-10 | 4.17 E-10 | 7.20 E-10 | 1.14 E-09 | 1.41 E-09 |
| 0.006 | 4.00 E-12 | 3.20 E-11 | 1.08 E-10 | 2.56 E-10 | 5.00 E-10 | 8.64 E-10 | 1.37 E-09 | 1.69 E-09 |
| 0.007 | 4.67 E-12 | 3.73 E-11 | 1.26 E-10 | 2.99 E-10 | 5.83 E-10 | 1.01 E-09 | 1.60 E-09 | 1.97 E-09 |
| 0.008 | 5.33 E-12 | 4.27 E-11 | 1.44 E-10 | 3.41 E-10 | 6.67 E-10 | 1.15 E-09 | 1.83 E-09 | 2.25 E-09 |
| 0.009 | 6.00 E-12 | 4.80 E-11 | 1.62 E-10 | 3.84 E-10 | 7.50 E-10 | 1.30 E-09 | 2.06 E-09 | 2.53 E-09 |
| 0.010 | 6.67 E-12 | 5.33 E-11 | 1.80 E-10 | 4.27 E-10 | 8.33 E-10 | 1.44 E-09 | 2.29 E-09 | 2.81 E-09 |
| 0.011 | 7.33 E-12 | 5.87 E-11 | 1.98 E-10 | 4.69 E-10 | 9.17 E-10 | 1.58 E-09 | 2.52 E-09 | 3.09 E-09 |
| 0.012 | 8.00 E-12 | 6.40 E-11 | 2.16 E-10 | 5.12 E-10 | 1.00 E-09 | 1.73 E-09 | 2.74 E-09 | 3.38 E-09 |
| 0.013 | 8.67 E-12 | 6.93 E-11 | 2.34 E-10 | 5.55 E-10 | 1.08 E-09 | 1.87 E-09 | 2.97 E-09 | 3.66 E-09 |
| 0.014 | 9.33 E-12 | 7.47 E-11 | 2.52 E-10 | 5.97 E-10 | 1.17 E-09 | 2.02 E-09 | 3.20 E-09 | 3.94 E-09 |
| 0.015 | 1.00 E-11 | 8.00 E-11 | 2.70 E-10 | 6.40 E-10 | 1.25 E-09 | 2.16 E-09 | 3.43 E-09 | 4.22 E-09 |

The distal end of cutter core wire 21 can have a reduced geometry. For optimal operation, the previous I and EI value ranges are preferable. Attached to the distal portion of the cutter core wire 21 is the cutter 40, and together they form a cutter assembly 58. At the point of attachment the solder is built up slightly to form a tapered connection to encourage thrombus to travel proximally.

Figure 8:
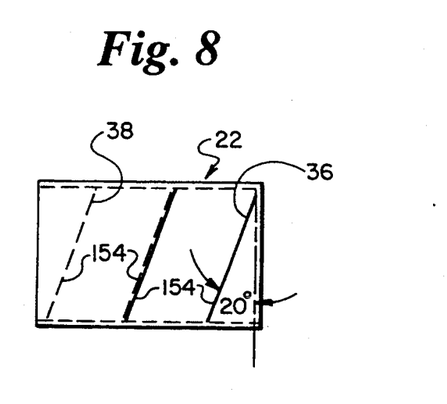
FIG. 8 is an enlarged isolated view of the distal housing of FIG. 7.

FIG. 8 is an isolated view of the distal housing 22. The distal housing is fabricated from a stainless steel tube about 0.110 inches long and having a wall thickness of about 0.0025 inches. Two, quadrilateral-shaped windows 36, 38 are formed in the cylindrical surface of the housing 22. Windows 36 and 38 are displaced 180 degrees from each other and are spaced along the longitudinal axis of the distal housing 22 such that the proximal edge of the distal window can overlap or be longitudinally spaced from the distal edge of the proximal window on the opposite side of the cylinder. The lateral edges 154 of windows 36 and 38 are at about a 20° angle to the longitudinal axis of the distal housing 22. It should be noted that corresponding windows are cut in the single-lumen tube 144 such that windows 36 and 38 open to the exterior of the thrombus extraction device 10.

Figure 9:
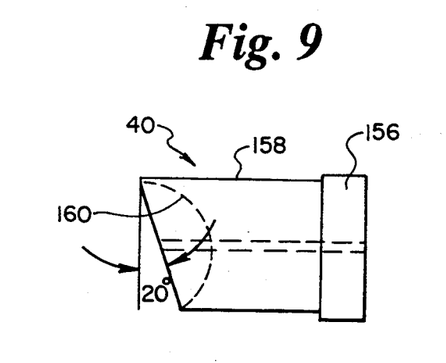
FIG. 9 is an enlarged side view of the cutter of FIG. 7.

FIG. 9 is a side view of the cutter 40 which is fabricated from a solid rod. Collar 156 is formed at the distal end of the cutter and has an outer diameter greater than the inner diameter of the distal housing 22 and approximately equal to the inner diameter of the single-lumen tube 144. The proximal cutter section 158 of the cutter 40 has a diameter that is about 0.0005 inches smaller than the inside diameter of the distal housing 22 such that the proximal cutter section 158 can slide with very little clearance into the distal housing 22. When the entire length of proximal cutter section 158 of the cutter is within the distal housing 22, the proximal edge of the collar 156 will engage the distal edge of the distal housing 22 thus stopping relative movement therebetween. The leading or proximal end of the cutter 40 is concave as shown at 160. The concavity 160 of the leading end provides a continuous cutting edge for the cutter 40. The leading face of the cutter is beveled at about a 20° angle to the cutter's longitudinal axis. The 20° angles of the windows' lateral edges and the leading face of the cutter are measured in opposite directions to produce a 40° angle between the cutting edges of the cutter 40 and the lateral edges 154 of windows 36 and 38.

Figure 10A:
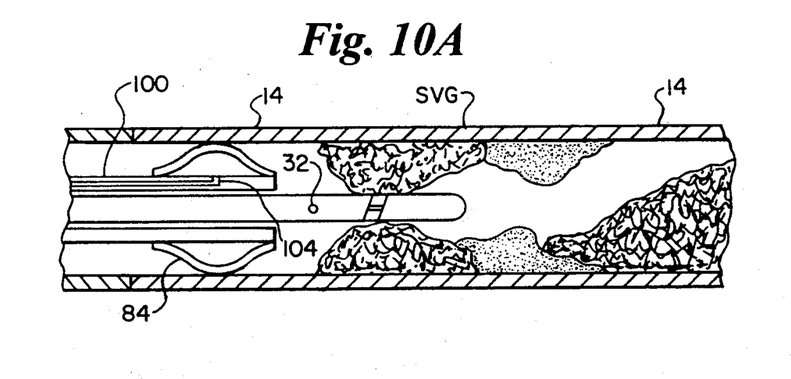
FIG. 10A is an illustration showing how the thrombus extraction device is positioned in the patient's vascular through a specialized guide catheter.
Figure 10B:
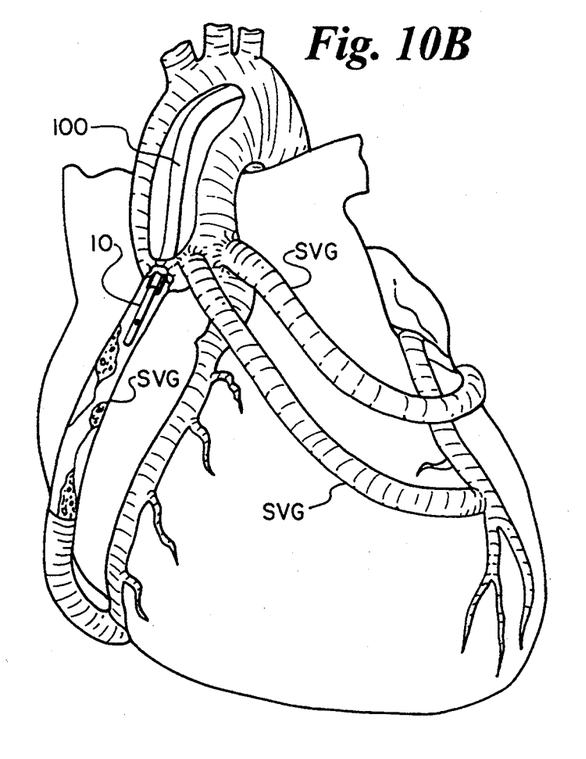
FIG. 10B is a perspective view of a heart that has several saphenous vein grafts with portions broken away to show the thrombus extraction device.

FIGS. 10A and 10B illustrate how the thrombus extraction device 10 is positioned in the patient's vascular system through a specialized guide catheter 100. In FIGS. 10A and 10B the fuzzy appearing material in the SVG represents thrombus and the solid black material represents stenotic lesions. The guide catheter 100 shown in this view is a guide catheter designed especially for this particular embodiment and need not be used for all embodiments of this invention. When the thrombus extraction device 10 emerges from the distal end of the guide catheter, it will be advanced into the saphenous vein graft. Guide catheter 100 has an inflatable balloon 84 secured to its outer surface at its distal end. An inflation lumen 104 extends through the wall of guide catheter 100 for inflating and deflating balloon 84.

The guide catheter 100 is introduced percutaneously through the femoral artery, brachial artery, or other suitable vascular. The guide catheter 100 is positioned with its distal tip in or near the ostia of the saphenous vein graft. The location of the vascular thrombus is identified either through angiographic techniques or by the use of external or intravascular ultrasound imaging.

The thrombus extraction device 10 must have sufficient longitudinal stiffness to be easily guided into the vascular system through the guide catheter 100 and sufficient flexibility to meet minimal resistance and not straighten or distort the guide catheter as it moves through it. There must be sufficient clearance between the thrombus extraction device 10 and the inside wall of guide catheter 100 to permit angiographic dye, irrigation fluids, or other fluids to be delivered through the annulus formed between the guide catheter and the thrombus extraction device 10.

The operation of the preferred embodiment thrombus extraction device in a saphenous vein graft application will now be discussed. In preparation of the patient for the thrombus extraction procedure, a guide catheter is inserted and properly positioned with the distal tip in or near the ostia of the graft or artery. The thrombus extraction device is then advanced in the guide catheter until the most distal tip emerges from the guide catheter into the vessel segment. Angiographic evaluation is performed by injection of radiopaque contrast through the guide catheter to determine the location of the thrombus. The thrombus extraction device is activated after the distal tip nears the location of the thrombus.

Effectiveness of the thrombus extraction device, for the preferred embodiment, depends on three separate mechanisms.

First, the application of the vacuum or negative pressure to the evacuation port 50 of the distal manifold 11 provides for a pressure differential that causes the thrombus constituents occupying the lumen of the vessel to be transported towards the windows 36, 38 of the thrombus extraction device and causes the fluid-thrombus mixture within the single lumen 162, distal tube 144, and/or distal housing 22 to flow proximally through lumen 30.

Second, once the thrombus enters a window 36 or 38 of the distal housing 22, a cutting apparatus positioned to move within the distal housing 22 in a predetermined motion sequence severs portions of the thrombotic material. The motion of the cutting apparatus and, more importantly, the irrigation fluid under pressure propels the severed pieces into the evacuation lumen 30 of the thrombus extraction device. The negative pressure differential between the proximal and distal segments of the thrombus extraction device contributes to the function of transporting the thrombotic material proximally to a collector 52 located external of the patient.

Third, the fluid injection mechanism permits the injection of sterile fluid, such as saline or thrombolytic, which establishes a flow pattern because of the pressure differential between the fluid introduction pathway and the evacuation lumen 30. This flow can be established within the catheter by introducing fluid exclusively through lumen 24; it can be established by creating a fluid flow that travels external of the thrombus extraction device; or a combination of internal and external flows can be established. This fluid introduction not only serves to effectively dilute the mixture of blood and thrombus and thereby modify the viscosity of the fluid but also effectively spaces the cut thrombus particles within the fluid mixture and "pushes" it proximally through 35 evacuation lumen 30. This spacing is a key element in preventing the thrombus evacuation device from clogging.

Sterile fluid can also be introduced within the blood vessel 14. This is accomplished by the introduction of fluids through an opening or openings 32 formed in lumen 24 at a location proximal of the distal housing 22. Thus, fluids exit the multi-lumen catheter body 20 through apertures 32 formed in the wall of first lumen 24. The fluids and thrombus are then drawn by the negative pressure internally of the distal housing 22 towards the windows 36, 38 formed in the walls of the distal housing 22. Alternately, fluid can also be introduced into the blood vessel through the annulus between the thrombus extraction device 10 and the guide catheter 100. When introducing irrigation fluid through the guide catheter, the fluid should have a pressure of about 300 millimeters of mercury above diastolic.

This introduction of fluid into the vessel 14 accomplishes four functions. First, it prevents the collapse of the vessel 14 around the thrombus extraction device. Such collapse would potentially damage the vessel. Second, the flow pattern established encourages the migration of thrombus towards the windows 36, 38 in the distal housing 22. Third, the fluid flow gently washes the wall of the vessel 14 and thereby improves the removal of thrombus as the thrombus and fluids are pulled toward windows 36, 38, and fourth, it reduces the amount of blood removed during the extraction procedure.

In order to prohibit the migration of thrombus into the vascular located distally of the thrombus extraction device during the procedure, it may be beneficial in some instances to temporarily eliminate perfusion of blood through the saphenous vein graft or vessel. Since the blood is flowing toward the distal end of the thrombus extraction device 10, this can be accomplished by blocking the flow of blood proximally of the site of the thrombus being extracted. Blocking the blood flow can be accomplished by placing an expandable occlusive apparatus, such as an expandable balloon 84, at the ostia of the bypass graft. The expandable balloon 84 may be associated with the guide catheter 100, as illustrated in FIG. 10A, or may be a separate restrictive member. Alternately, occlusion may be accomplished by mechanically expandable members integrated on the guide catheter or as a parallel mechanical or hydraulic mechanism, such as a balloon catheter. This procedure, of blocking the flow of blood over the thrombus extraction catheter will prevent thrombus particles from flowing into the arterial vessels or further into the capillary bed which separates the arterial and venous systems. If particles were to effectively migrate into the smaller vessels and occlude them, these vessels would have a tendency to completely close due to thrombosis. This would greatly offset, if not eliminate altogether, the benefit of the thrombus extraction procedure.

Another embodiment of the thrombus extraction device differs from the preferred embodiment in that the opening or openings 32 formed in the wall of the lumen 24 have been eliminated. Within this embodiment two options are available, the first being that the negative pressure exerted through lumen 30 functions to pull the thrombus through the window or windows of the distal housing 22 and all dilution of the thrombus occurs within single lumen 162. The second option is to supply additional irrigation fluid through the guide catheter 100 which can mix with the blood and thrombus prior to being pulled through the window or windows formed in the distal housing.

Alternately, sterile fluids can be introduced simultaneously within and outside the thrombus extraction device and return via windows 36 or 38 and lumen 30.

Figure 11A:
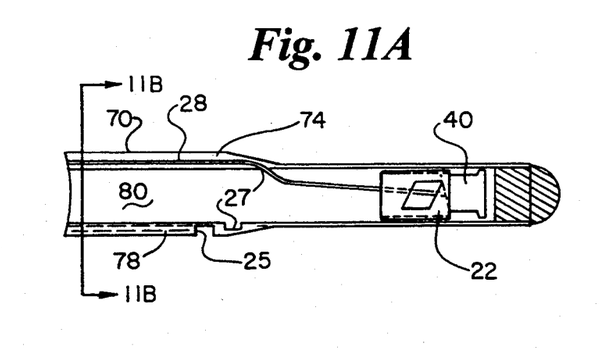
FIG. 11A is a cross-sectional side view of another embodiment of a multi-lumen catheter body.
Figure 11B:
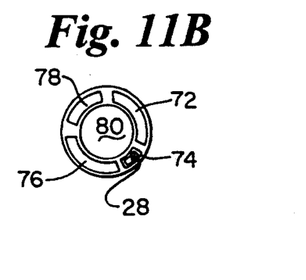
FIG. 11B is a cross-sectional view of the catheter body taken along lines 11B—11B of FIG. 11.

FIG. 11A and 11B show another embodiment of a multi-lumen catheter body 70. As best seen in FIG. 11B, this embodiment has a plurality of radial lumens 72, 74, 76 and 78 that surround a central evacuation lumen 80. Central evacuation lumen 80 extends from port 50 of the distal manifold 11 to the distal extremity of the thrombus extraction device 10. The radial lumens 72, 74, 76 and 78 provide the dual functions, either separately or in combination, of delivering fluid to the distal end of the thrombus extraction device 10 and of housing the flexible elongated member 28 that transmits movement to the cutter 40. Fluid can be delivered through radial lumens 72, 74, 76 and 78 from port 46 of the proximal manifold 17 into the patient's vessel 14 through an opening or openings 25 formed in the thrombus extraction device's outer wall and/or into the central evacuation lumen 80 through opening or openings 27. The combined slurry created by the infusion of fluid and fragmented thrombus into the distal extremity of evacuation lumen 80 is vacuum extracted through evacuation lumen 80 through port 50 into the fluid collector 52.

Figures 12, 13, 14A:
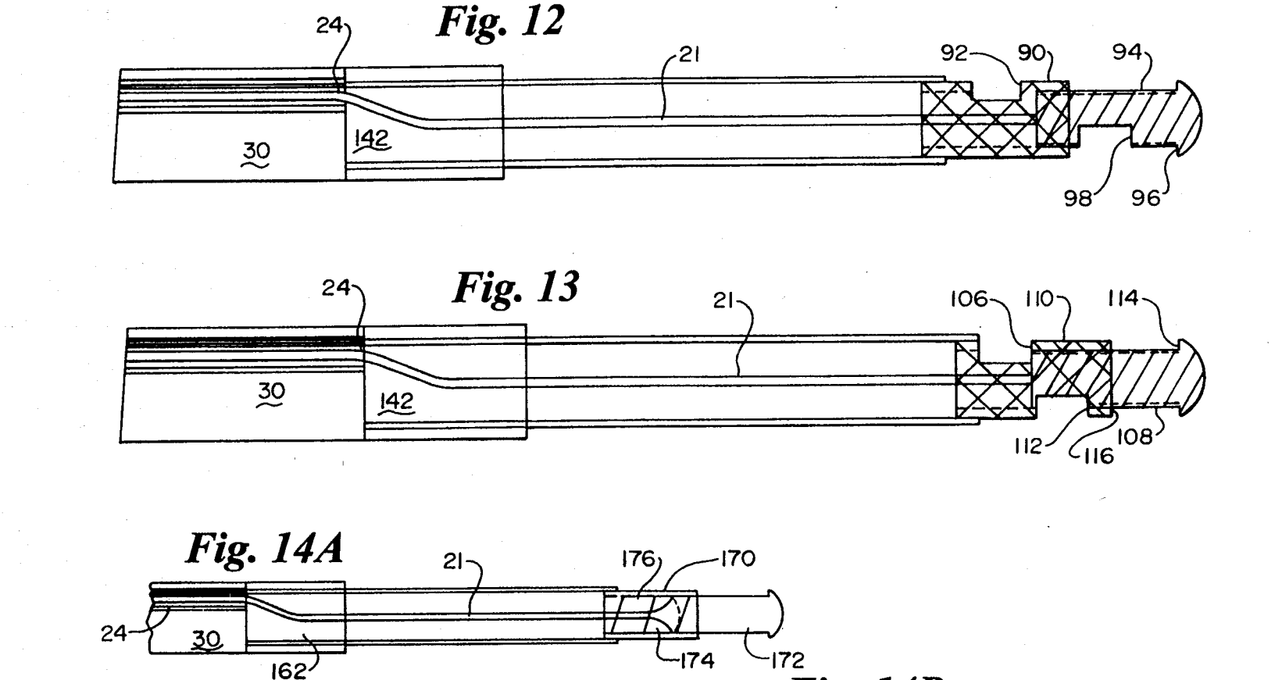
FIG. 12 is a side view of another embodiment of the distal housing and cutter.
FIG. 13 is a side view of another embodiment of the distal housing and cutter.
FIG. 14A is a side view of another embodiment of the distal housing and cutter.

FIG. 12 illustrates a thrombus extraction catheter that functions similarly to those embodiments described above, except that in this embodiment the distal end of the cutter 94 protrudes from the distal end of the housing 90 during the cutting stroke. In this embodiment thrombus is drawn into the distal housing 90 through a window 92 formed in the distal housing, and thrombus is also engaged by window 98 formed in cutter 94. Window 98 is located approximately on the opposite side of the device from window 92. A stop 96 is provided at the distal end of cutter 94 that engages the distal end of distal housing 90 when the cutter 94 reaches the end of its stroke in the proximal direction. A cutter stop 97 may also be provided in the housing to stop cutter 94 as it reaches the end of its stroke in the distal direction. When the cutter 94 is in the location illustrated in FIG. 12, thrombus is pulled into the housing 90 and cutter 94 through windows 92, 98. When cutter 94 moves proximally the thrombus that has been pulled into the chamber through windows 92 and 98 is sheared off by the cooperating edges of the distal housing 90 and the cutter 94. In this embodiment fluid pathways can also be established either internally, externally, or both internally and externally of the catheter body.

FIG. 13 illustrates a thrombus extraction catheter which provides for a construction in which the thrombus is drawn into the distal housing 110 through windows 106 and 112 formed therein. Windows 106 and 112 are located approximately on opposite sides of the distal housing and may be spaced longitudinally such that the two windows preferably do not overlap. When the cutter 108 is protruded from the distal-most extremity of the distal housing 110, both windows 106 and 112 are open to the outside of the catheter such that thrombus is drawn into the chamber within distal housing 110 by the negative pressure that is applied to lumen 30. The thrombus is cut by the proximal end of the cutter 108 as the cutter 108 is drawn into the housing in the proximal direction. The cutter 108 35 includes a peripheral stop 114 that engages the distal end 116 of distal housing 110 when it reaches the end of its stroke in the proximal direction, and a cutter stop 115 may also be provided in the housing to stop cutter 108 as it reaches the end of its stroke in the distal direction. In this embodiment, also, fluid pathways can be established either internally, externally, or both internally and externally of the catheter body.

Figure 14B:
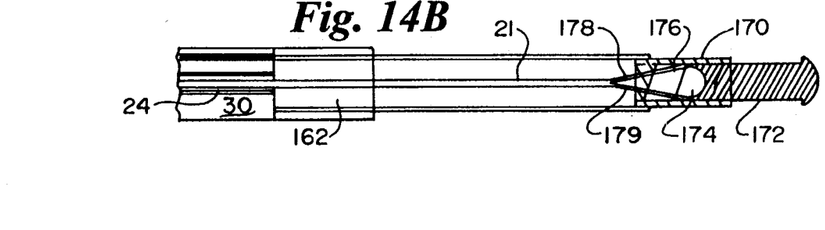
FIG. 14B is a top view of the distal housing and cutter seen in FIG. 14A.

FIGS. 14A and 14B illustrate another alternative embodiment of the thrombus extraction catheter which provides for a construction in which the thrombus is drawn into the distal housing 170 through windows 174, 176. Windows 174 and 176 are located approximately on opposite sides of the distal housing 170 and are spaced longitudinally such that the two windows preferably do not overlap. In this embodiment, the cutter 172 is protruded from the distal-most extremity of the distal housing 170. The shape of the cutter provides for the thrombus to be located in adjacent areas in the chamber that is within the distal housing 170 when the cutter is extended. The thrombus is cut as the cutter is drawn into the housing. In this embodiment the cutter core wire 21 divides into two sections 178 and 179 at its distal end. The distal ends of sections 178 and 179 are secured to opposite sides of cutter 172 which functions to add stability to the movement transmitted to the cutter 172 by the cutter core wire 21.

Figure 15A:
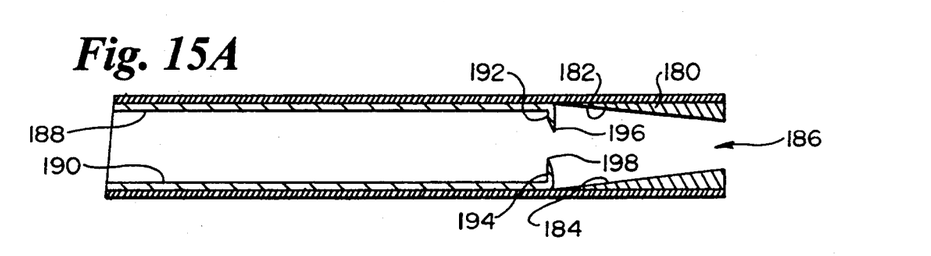
FIG. 15A is a side view of another embodiment of the distal housing and cutter with the cutter positioned such that the window of the distal housing is open.
Figure 15B:
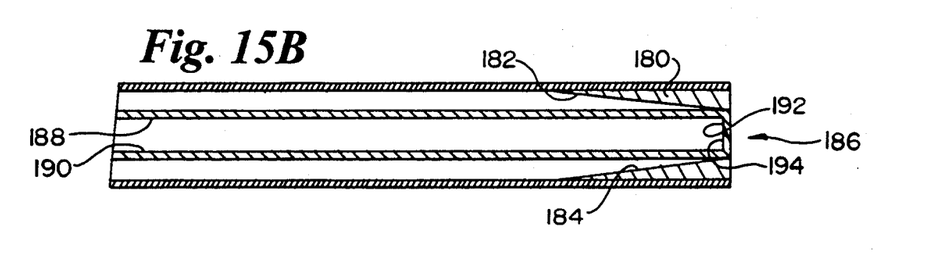
FIG. 15B is a side view of the embodiment of the distal housing and cutter seen in FIG. 15A with the cutter positioned such that the window of the distal housing is closed.

FIGS. 15A and 15B illustrate the distal portion of a thrombus extraction catheter, which provides for a construction in which the distal housing 180 can either be formed of a pair of converging beveled surfaces 182 and 184 within its internal chamber or of a tubular element with a conical inner surface that narrows distally. The beveled surfaces 182 and 184 converge toward a window 186 formed in its distal most end of distal housing 180. The cutter of this embodiment includes two elongated members 188 and 190 that have right-angle portions 192, 194 at their distal ends. Elongated members 188 and 190 may be attached to cutter core wire 21. The right-angle portions 192, 194 terminate in beveled cutting edges 196, 198. As best seen in FIG. 15A when elongated members are in their proximal position, the window 186 is open and thrombus can be pulled into the internal chamber of the distal housing 180 by negative pressure transmitted through lumen 30. At the appropriate time in the thrombus extraction process the elongated members 188 and 190 are caused to move in the distal direction. During this movement the elongated members 188 and 190 engage the beveled surfaces 182 and 184 causing beveled cutting edges 196, 198 to close and sever the thrombus that has been pulled into the chamber from the thrombus that is outside the catheter. The beveled cutting edges 196, 198 are shown closed in FIG. 15B. The severed thrombus along with fluids from outside or inside the catheter are then extracted from the closed chamber through extraction lumen 30 in a manner similar to that described above in the preferred embodiment.

Figure 16A:
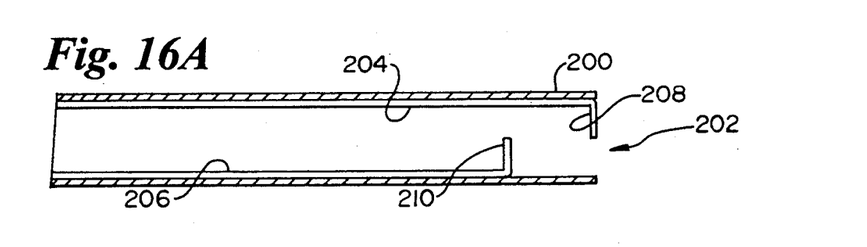
FIG. 16A is a side view of another embodiment of the distal housing and cutter elements with the cutter elements located such that the window of the distal housing is open.
Figure 16B:
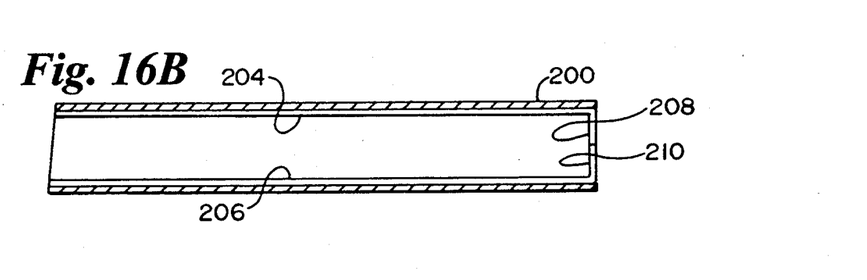
FIG. 16B is a side view of the embodiment of the distal housing and cutter elements seen in FIG. 16A with the cutter elements located such that the window of the distal housing is closed.
Figure 16C:
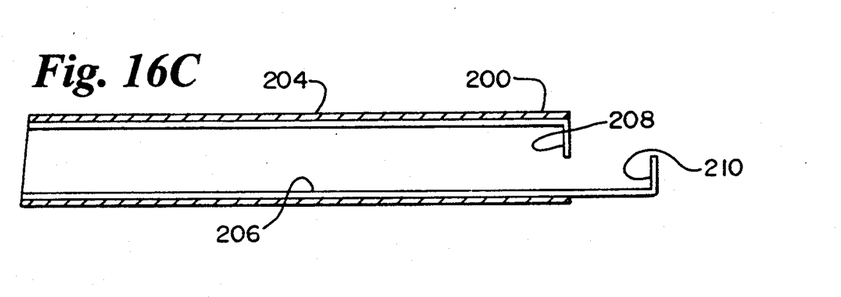
FIG. 16C is a side view of the embodiment of the distal housing and cutter elements seen in FIG. 16A with the cutter elements located such that the window of the distal housing is open.

FIGS. 16A, 16B, and 16C illustrate the distal portion of a thrombus extraction catheter which provides for a construction in which the distal extremity of the distal housing 200 is open and functions as a window 202. The cutter is constructed of two separate parts 204 and 206 that may be formed of round or flat wires or of a longitudinally split tubing. The cutter parts 204, 206 have right-angle portions 208 and 210 at their distal ends.

In a first version of this embodiment cutter part 204 is stationary and cutter part 206 reciprocates in the longitudinal direction. In the position shown in 16A thrombus can be pulled through window 202 into the chamber of the distal housing 200 by the negative pressure supplied through lumen 30. When the cutter part 206 then moves to the position shown in FIG. 16B, the right-angle portions 208 and 210 are adjacent and cooperate to sever the thrombus that has entered the chamber. Also at this point in the cycle the window 202 has been closed. The cutter part 206 then moves from its position in FIG. 16B to its position shown in FIG. 16C. When the cutter part 206 is in this position, the window 202 is again open and thrombus can be pulled into the chamber by the negative pressure from lumen 30. The cutter part 206 then moves from its position shown in FIG. 16C back to its position shown in FIG. 16B, at which position the thrombus that has been pulled into the chamber is severed and is free to be carried away with the fluid through lumen 30.

In the second version of this embodiment both cutter parts 204 and 206 are reciprocated in a timed relationship such that the right-angle portions 208 and 210 become aligned as illustrated in FIG. 16B at the beginning and the end of each cycle. Referring to FIG. 16B as the beginning of a cycle, the cutter parts 204 and 206 move in opposite directions which results in the window 202 opening so that thrombus can be pulled into the chamber. Both cutter parts 204 and 206 then stop and reverse directions, returning to the positions shown in FIG. 16B, causing the window 202 to be closed and the thrombus severed. The cutter parts 204 and 206 then move away from the FIG. 16B position in the opposite directions that they moved at the beginning of the cycle, again opening the window 202, and then returning to the FIG. 16B position where the thrombus is again severed and the cycle has been completed.

Figure 17:
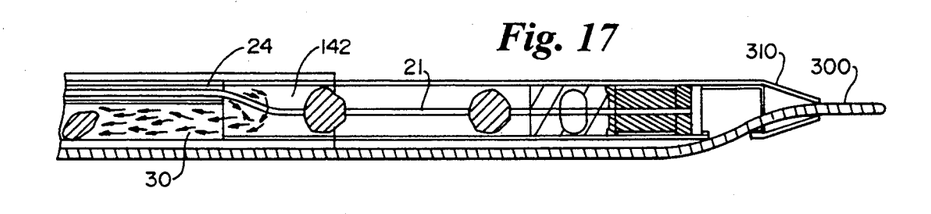
FIG. 17 is a side view of another embodiment of the thrombus extraction device used in cooperation with a guide wire.

FIG. 17 illustrates an embodiment showing the thrombus extraction device in cooperation with a guide wire 300. This embodiment has particular application for removing thrombus from the peripheral or coronary arterial vascular system. In this embodiment, a specialized tip 310 is attached to the distal end of thrombus extraction device 10 to receive the guide wire 300, which is carried substantially parallel to and external of the device. Alternately, a separate lumen can be provided internally for the passage of the guidewire 300.

Figure 18:
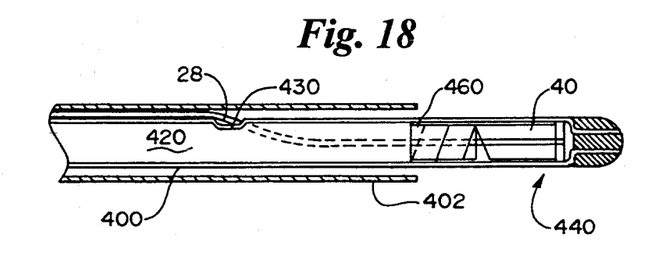
FIG. 18 is a side view of another embodiment of the thrombus extraction device having a single lumen.

FIG. 18 illustrates another embodiment of the thrombus extraction device in which the catheter body 400 is comprised of a single lumen 420 to which vacuum or negative pressure is applied. In this embodiment, the flexible elongated member 28 extends mostly parallel to and outside the catheter body 400 for substantially the entire length of the catheter and passes through port 430 into the distal region 440 of the catheter body 400 where it is attached to the cutter 40. This embodiment provides for a smaller catheter body design because the flexible elongated member 28, which includes the cutter core wire 21, can be accommodated in the annulus formed between the guide catheter 402 and the device without increasing the size of the guide catheter. This annulus also allows for the introduction of sterile fluid into the vessel. If the catheter body 400 is composed of composite materials, the distal housing 460 may be functionally replaced by varying the composite material along the catheter body.

It is intended that the accompanying drawings and foregoing detailed description is to be considered in all respects as illustrative and not restrictive. The scope of the invention is intended to embrace any equivalents, alternatives, and/or modifications of elements that fall within the spirit and scope of the invention, and all changes which come within the meaning and range of equivalency of the claims are therefore intended to be embraced therein.

What is claimed is:

1. A method of removing a thrombus from a saphenous vein graft comprising the steps of:
    (a) diluting the thrombus in the saphenous vein graft with fluid introduced into the patient's vessel adjacent the saphenous vein graft;
    (b) aspirating the diluted thrombus and fluid through a window formed in a distal single-lumen region located at the distal end portion of a catheter that has been placed in the saphenous vein graft of a patient;
    (c) severing the thrombus within the distal single-lumen region from thrombus outside the catheter at the window;
    (d) transporting the severed thrombus particles and fluid out of the distal single-lumen region by applying negative pressure at the proximal end of a lumen, that communicates with the distal single-lumen region, at the distal end portion of the catheter.

2. A method as recited in claim 1, in which the fluid introduced into the patient's vessel in step (a) is introduced through the annulus formed between a guide catheter and the catheter.

3. A method as recited in claim 2, including the additional step of:
    restricting the blood flow in the patient's vessel proximal of the distal end of the guide catheter to prevent its flow in the distal direction.

4. A method as recited in claim 1, including the additional step of:
    restricting the blood flow in the patient's vessel proximal of the saphenous vein graft to prevent its flow in the distal direction.

5. In an thrombus extraction device comprising a multi-lumen catheter body having a proximal end portion and a distal end,
    said multi-lumen catheter body opening up into a single-lumen body at its distal section,
    a window formed in the single-lumen body section,
    a cutter mounted for movement in said single-lumen body, past said window, to a distal position at which it protrudes from the distal end of said single-lumen body,
    an elongated flexible member extending from said proximal end portion of the multi-lumen catheter body to said cutter for transmitting movement to said cutter from the proximal end portion of the multi-lumen catheter body,
    a fluid supply and pressure means for supplying fluid under pressure to a first lumen of said multi-lumen catheter body to cause fluid to flow to the distal end of said multi-lumen catheter body,
    a vacuum source connected to a second lumen of said multi-lumen catheter body for supplying a negative pressure to the second lumen and causing fluid carrying cut thrombus particles to flow proximally from said single-lumen body through said second lumen to the proximal end portion of said multi-lumen catheter body.

6. In an thrombus extraction device comprising a multi-lumen catheter body having a proximal end portion and a distal end portion, a chamber at the distal end portion of the catheter body in fluid communication with said multi-lumens and a window formed in the chamber, the improvement comprising:
    a cutter element mounted in the chamber for axial movement past the window, said cutter element defining a sharpened cutting edge oriented to sever material which is extending through the window as the cutter element moves axially past the window;
    a flexible elongated member extending from the proximal end portion of the catheter body through one of its lumens and connected to said cutter element for transmitting movement to said cutter;

controllable fluid pressure means connected to one of the catheter body's lumens, causing fluid under pressure to flow from the proximal end portion of said thrombus extraction device through said one of the catheter body's lumens toward said proximal end portion where it flows into said chamber, an opening formed in the distal end portion of said catheter body, proximal said chamber and opening into the lumen through which fluid under pressure is flowing, through which the fluid under pressure can escape to the exterior of said thrombus extraction device, controllable vacuum producing means, connected to another of the catheter body's lumens at its proximal end portion, such that fluid supporting portions of the severed thrombus particles flows proximally from within the chamber through said another of the catheter body's lumens.

7. A method of removing a thrombus from the peripheral or coronary vascular system comprising the steps of:
   (a) diluting the thrombus in the peripheral or coronary vascular system with fluid introduced into the patient's vessel adjacent the thrombus site in the peripheral or coronary vascular system;
   (b) aspirating the diluted thrombus and fluid through a window formed in a distal single-lumen region located at the distal end portion of a catheter that has been placed in the peripheral or coronary vascular system of a patient;
   (c) severing the thrombus within the distal single-lumen region from thrombus outside the catheter at the window;
   (d) transporting the severed thrombus particles and fluid out of the distal single-lumen region by applying negative pressure at the proximal end of a second lumen, that communicates with the distal single-lumen region, at the distal end portion of the catheter.

8. A method as recited in claim 7, in which the fluid introduced into the patient's vessel in step (a) is introduced through the annulus formed between a guide catheter and the catheter.

9. A method as recited in claim 8, including the additional step of:
   restricting the blood flow in the patient's vessel proximal of the distal end of the guide catheter to prevent its flow in the distal direction.

10. A method as recited in claim 7, including the additional step of:
    restricting the blood flow in the patient's vessel proximal of the thrombus site in the peripheral or coronary vascular system to prevent its flow in the distal direction.

11. A method as defined in claim 7 wherein prior to step (a) the following steps are performed:
    percutaneously introducing a guide wire and guide catheter into the patient's vascular system such that the guide wire extends through the guide catheter into the cite of the thrombus; and
    attaching the thrombus extraction device to the guide wire externally of the patient.

12. A method as defined in claim 11 in which the guide wire is attached to the thrombus extraction device by being threaded through an opening that extends from the most distal portion of its tip to the side of its tip.

* * * * *